(12) United States Patent
Sun et al.

(10) Patent No.: US 8,990,023 B2
(45) Date of Patent: Mar. 24, 2015

(54) HIGH-THROUGHPUT AUTOMATED CELLULAR INJECTION SYSTEM AND METHOD

(76) Inventors: Yu Sun, Toronto (CA); Wenhui Wang, Toronto (CA); Xinyu Liu, Toronto (CA)

( * ) Notice: Subject to any disclaimer, the term of this patent is extended or adjusted under 35 U.S.C. 154(b) by 1296 days.

(21) Appl. No.: 11/678,608

(22) Filed: Feb. 25, 2007

(65) Prior Publication Data

US 2008/0077329 A1 Mar. 27, 2008

(30) Foreign Application Priority Data

Sep. 21, 2006 (CA) .................................. 2560352

(51) Int. Cl.
*C12M 1/00* (2006.01)
*G01N 35/10* (2006.01)
*C12M 1/42* (2006.01)
*C12M 1/36* (2006.01)

(52) U.S. Cl.
CPC ............... *C12M 23/50* (2013.01); *C12M 35/00* (2013.01); *C12M 41/48* (2013.01)
USPC ............ 702/19; 435/6.1; 435/285.1; 435/455

(58) Field of Classification Search
CPC ...... C12M 35/00; C12M 21/06; C12M 23/16; C12M 33/04; C12M 35/02; C12M 35/04; C12M 41/12; C12M 23/10; C12M 23/50; C12M 25/06
USPC .......................................................... 702/19
See application file for complete search history.

(56) References Cited

U.S. PATENT DOCUMENTS

| | | | | |
|---|---|---|---|---|
| 5,262,128 | A | * | 11/1993 | Leighton et al. ............... 422/522 |
| 5,310,674 | A | * | 5/1994 | Weinreb et al. ............ 435/286.1 |
| 5,457,041 | A | | 10/1995 | Ginaven |
| 5,665,591 | A | * | 9/1997 | Sonenshein et al. ........... 435/375 |
| 5,998,697 | A | * | 12/1999 | Devlin ............................. 800/20 |
| 6,558,361 | B1 | | 5/2003 | Yeshurun |
| 2004/0235143 | A1 | | 11/2004 | Sasaki et al. |
| 2005/0250197 | A1 | * | 11/2005 | Ando et al. ................. 435/285.1 |
| 2006/0183215 | A1 | | 8/2006 | Youoku et al. |
| 2007/0048857 | A1 | | 3/2007 | Ito et al. |

FOREIGN PATENT DOCUMENTS

EP 0463508 A1 * 1/1991

OTHER PUBLICATIONS

Pepperkok et al., 1991, Cytotechnology, 5: S93-98.*
Pepperkok et al., 1998, PNAS, USA, 85: 6748-6752.*
Golden et al., 2002, Biosensors and Bioelectronics, 17: 719-725.*
Yamamoto et al., 2002, IEEE Transactions on Instrumentation and Measurement, 51: 182-187.*
Lukkari et al., Jun. 2005, Proceedings 2005 IEEE International Symposium on Computational Intelligence in Robotics and Automation, pp. 701-706.*
Amsterdam et al., 1999, Genes and Development, 13: 2713-2724.*
Dictionary definition for reservoir [online], 2010 [retrieved on Mar. 29, 2010]. Retrieved from the Internet:< URL: http://dictionary.reference.com/browse/reservoir>, pp. 1-5.*
Sun et al. "Biological Cell Injection Using an Autonomous MicroRobotic System." The International Journal of Robotics Research, vol. 21, No. 10-11, pp. 861-868, 2002.*
Yu et al. "Autonomous Injection of Biological Cells Using Visual Servoing." Experimental Robotics VII, LNCIS 271, pp. 169-178, 2001.*
Pillarisetti et al. "Evaluating the Role of Force Feedback for Biomanipulation Tasks." Haptic Interfaces for Virtual Environment and Teleoperator Systems Conference Proceedings, pp. 11-18, Mar. 25-26, 2006.*
Sun et al. "Biological Cell Injection Using an Autonomous MicroRobotic System." The International Journal of Robotics Research (2002) vol. 21, No. 10-11, pp. 861-868.*
Nelson et al. "Microrobotics for Molecular Biology: Manipulating Deformable Objects at the Microscale." Robotics Research, 2005. STAR 15, pp. 115-124.*
Pillarisetti et al. "Evaluating the Role of Force Feedback for Biomanipulation Tasks." Symposium on Haptic Interfaces for Virtual Environment and Teleoperator Systems Mar. 25-26, 2006, Proceedings, pp. 1-11.*
Definition of automated, website (http://www.merriam-webster.com/) accessed Feb. 18, 2014.*
R. Kumar, A. Kapoor, and R.H. Taylor "Preliminary experiments in robot/human cooperative microinjection," Proc. IEEE International Conf. on Intelligent Robots and Systems, pp. 3186-3191, Las Vegas, 2003.
H. Matsuoka, T. Komazaki, Y. Mukai, M. Shibusawa, H. Akane, A. Chaki, N. Uetake, and M. Saito, "High throughput easy microinjection with a single-cell manipulation supporting robot," J. of Biotechnology, vol. 116, pp. 185-194, 2005.

(Continued)

*Primary Examiner* — Thaian N Ton
*Assistant Examiner* — Titilayo Moloye
(74) *Attorney, Agent, or Firm* — Eduardo Krupnik; Miller Thomson LLP

(57) ABSTRACT

An automated cell injection system and method are described, which can perform automatic, reliable, and high-throughput cell injection of foreign genetic materials, proteins, and other compounds. The system and method overcome the problems inherent in traditional manual injection that is characterized by poor reproducibility, human fatigue, and low throughput. The present invention is particularly suited for zebrafish embryo injection but can be readily extended to other biological injection applications such as mouse embryo, *drosophila* embryo, and *C. elegans* injections, capable of facilitating high-throughput genetic research at both academic and industry levels. A novel vacuum based cell-holding device is also provided.

23 Claims, 12 Drawing Sheets

(56) References Cited

OTHER PUBLICATIONS

Y. Sun and B.J. Nelson, "Biological cell injection using an autonomous microbotic system," Int. J. of Robot. Res., vol. 21, pp. 861-868, 2002.

S. Zappe, M. Fish, M.P. Scott, and O. Solgaard, "Automated MEMS-based *Drosophila* embryo injection system for high-throughput RNAi screens," Lap Chip, vol. 6, pp. 1012-1019, 2006.

www/multichannelsystems.com/products/roboocyte/robohardware/robohardwareinto.htm.

K. Chun, G. Hashiguchi, H. Toshiyoshi, H. Fujita, Y. Kikuchi, J. Ishikawa, Y. Murakami, and E. Tamiya, "An array or hollow microcapillaries for the controlled injection of genetic materials into animal/plant cells," in Proc. IEEE Conf. MEMS, 1999, pp. 406-411.

\* cited by examiner (a)

(b)

(c)

(d)

(e)

(f)

(g)

(h)

HIGH-THROUGHPUT AUTOMATED CELLULAR INJECTION SYSTEM AND METHOD

This application claims the benefit of Canadian Patent Application No. 2,560,352, filed 21 Sep. 2006.

FIELD OF THE INVENTION

The present invention relates to cell manipulation, automation, micromanipulation and microrobotics.

BACKGROUND OF THE INVENTION

Recent advances in molecular biology, such as the creation of transgenic organisms, demonstrate that increasingly complex micromanipulation strategies are required for manipulating individual biological cells. In order to create transgenic organisms such as those for cancer studies, genetic materials need to be injected into cells. Conventionally, cell injection has been conducted manually; however, long training, low throughput, and low success rates from poor reproducibility in manual operations call for the elimination of direct human involvement and fully automated injection systems.

The zebrafish has emerged as an important model organism for development and genetic studies, due to the similarities in gene structures to the human being, external fertilization and development, short development period, and the transparency of embryos making it easy to observe the fate of individual cells during development. The recent growth in the number of laboratories and companies using zebrafish in vertebrate developmental genetics has been exponential. The injection of thousands of zebrafish embryos is required on a daily basis in a moderate-sized zebrafish genetics laboratory/company, for applications such as embryonic development studies and mutation screening to identify genes. The laborious manual injection task easily causes fatigue in injection technicians and hinders performance consistency and success rates. The current manual technology is not capable of meeting the needs of such high-throughput applications.

Currently, no automated, high-throughput zebrafish embryo injection systems are available. Many attempts have been made to leverage existing technologies, such as microrobotics and MEMS (microelectromechanical systems), to facilitate the process of cell injection. Microrobot-assisted (i.e. teleoperated) cell injection systems have been developed, where microrobots/micromanipulators are controlled by the operator to provide "steady hand" and conduct "human-in-loop" cell injections. (See R. Kumar, A. Kapoor, and R. H. Taylor, "Preliminary experiments in robot/human cooperative microinjection," Proc. IEEE International Conf. on Intelligent Robots and Systems, pp. 3186-3191, Las Vegas, 2003; and H. Matsuoka, T. Komazaki, Y. Mukai, M. Shibusawa, H. Akane, A. Chaki, N. Uetake, and M. Saito, "High throughput easy microinjection with a single-cell manipulation supporting robot," *J. of Biotechnology*, Vol. 116, pp. 185-194, 2005.) Although the microrobots can to a certain extent facilitate cell injection by a human operator without long training, the human involvement still exists in the process of cell injection, resulting in a low throughput and reproducibility.

A visually servoed microrobotic mouse embryo injection system has been developed, using a holding micropipette for immobilizing a single mouse embryo, and a visually servoed microrobot for automated cell injection. (See Y. Sun and B. J. Nelson, "Biological cell injection using an autonomous microrobotic system," *Int. J. of Robot. Res.*, Vol. 21, pp. 861-868, 2002.) However, switching from one embryo to another was conducted manually, and thus, injection was time consuming.

A semi-automated MEMS-based high-throughput *drosophila* embryo injection system was reported recently, where a MEMS microneedle was used as an injector. (See S. Zappe, M. Fish, M. P. Scott, and O. Solgaard, "Automated MEMS-based *drosophila* embryo injection system for high-throughput RNAi screens," Lap Chip, Vol. 6, pp. 1012-1019, 2006.) A 3-DOF scanning stage was used for locating randomly dispersed embryos that were 'glued' on a glass slide, and another 3-DOF motion stage with the injector mounted was employed for injection. One drawback of this system is that manual alignment of the two stages was required before injection. The large alignment error would greatly influence the injection performance. More importantly, the low stiffness of the MEMS injector requires that the hard embryo chorion be removed in order to facilitate the injection, which may affect subsequent embryonic development, making the system unsuitable for zebrafish or mouse embryo injection. Additionally, randomly dispersing embryos slows down the injection speed due to the embryo searching process.

A commercial cell injection system has been developed for oocyte injection of *Xenopus laevis* (frog), where oocytes are manually loaded into a standard 96 well plate, an x-y stage is responsible for positioning target cell to the operation area, and a z-motor with an injection micropipette mounted conducts cell injection (ROBOOCYTE™ by Multi Channel Systems MCS GmbH). In this system, introducing oocytes into regular patterned wells is conducted manually, which is tedious and time consuming. The injection accuracy was sacrificed due to the open-loop operation. Without feedback, such as vision, integrated into the control system to improve the positioning accuracy and monitor the injection process, the injection performance is sacrificed and robustness not warranted.

U.S. Patent Application No. 20050250197 to Ando et al. discloses a microinjection apparatus and corresponding operation methods. A silicon microfabricated device integrating suction holes is proposed for cell trapping. The deformation of the thin silicon membrane due to an applied suction pressure is compensated for by measuring the height of the membrane with a detection-mark focusing technique. The silicon substrate is not optically transparent, making the observation, monitoring, and control of the injection process difficult.

U.S. Patent Application No. 20050250197 also proposes two methods for measuring the vertical distance between the micropipette tip and substrate surface, using the mirror effects of well-polished silicon surface. The methods intend to determine the height information by focusing on certain features, which will be effective only when the depth of focus is small. However, the size of zebrafish embryos requires a relatively low microscopy magnification that inherently has a large depth of focus (hundreds of micrometers). Thus, the detection methods proposed are not suitable to use for zebrafish embryo injection.

Targeting high-throughput cell injection, MEMS-based microneedle arrays have been developed to perform parallel cell injection. The paper "An array of hollow micro-capillaries for the controlled injection of genetic materials into animal/plant cells" (K. Chun, G. Hashiguchi, H. Toshiyoshi, H. Fujita, Y. Kikuchi, J. Ishikawa, Y. Murakami, and E. Tamiya, in Proc. IEEE Conf. MEMS, 1999, pp. 406-411) describes a microneedle array-based cell injection system, including a microneedle array injector and a microchamber array for cell trapping.

U.S. Pat. No. 5,262,128 to Leighton et al., U.S. Pat. No. 5,457,041 to Ginaven et al., and U.S. Pat. No. 6,558,361 to Yeshurun also disclose microneedle array designs for cell injection use. Although the concept of using microneedle arrays for parallel cell injection is appealing, solutions to several critical issues do not exist. First, precisely aligning microneedles with regularly positioned cells is difficult. Manual alignment (in-plane or x-y alignment) through microscopic observation from an off-optical-axis angle cannot guarantee a high accuracy. Second, determining the vertical distance (out-of-plane or z) between microneedle tips and cells is difficult. Size differences from one cell to another (e.g., zebrafish embryos can differ by 200-300 cm) make vertical alignment/positioning impossible. Automation is not an option. Third, particularly for zebrafish embryo injection, the size of zebrafish embryos requires microneedles with a tip length of ~600 μm and outer diameter of 5-10 μm throughout the 600 μm length. The injection needles also must be strong enough without buckling under hundreds of microNewton penetration forces during zebrafish embryo injection. These requirements for microneedles make the selection of MEMS-based solutions inappropriate. In summary, parallel injection with MEMS microneedle arrays is not applicable to zebrafish embryo injection.

It should be understood that despite their relatively large size (~600 μm and ~1.2 mm including chorion), zebrafish embryos have a delicate structure and can be easily damaged. They are also highly deformable, making the automatic manipulation task difficult. Therefore specific difficulties in achieving automated zebrafish embryo injection include: (i) the ability to quickly (i.e. seconds) immobilize a large number of zebrafish embryos into a regular pattern; (ii) the ability to automatically and robustly identify cell structures for vision-based position control (i.e. visual servoing) and account for size differences across embryos; and (iii) the ability to co-ordinately control two motorized positioning devices to achieve robust, high-speed zebrafish embryo injection.

In view of the foregoing, what is needed is a system and method for cellular injection that overcomes the limitations of the prior art, such that the system and method feature automation, robustness, high-throughput (including sample positioning), high success rates, and high reproducibility.

SUMMARY OF THE INVENTION

In one aspect, the present invention is a system for automated cellular injection comprising: a first positioner control device operable to control motion of a first positioner, the first positioner connected to a holding device operable to immobilize one or more cells in a desired position, the one or more cells including a target cell; a second positioner control device operable to control motion of a second positioner, the second positioner connected to an injection means, the injection means having a tip; a pressure unit connected to the injection means, the pressure unit operable to pass a desired deposition volume of a material at a desired injection pressure to the injection means; and a microscope means for viewing the position of the injection means relative to the holding device; wherein the first positioner control device, the second positioner control device, the pressure unit and the microscope means are linked to a host computer, the host computer including control software for motion control and image processing that enables a user to inject the material into the target cell through the tip of the injection means.

In another aspect, the present invention is a method for automated cellular injections comprising immobilization, control sequence, and computer vision recognition. According to this method, a number of cells are positioned on a holding device and viewed through a microscope means. Each cell is recognized and centered in the field of view, and the injection means tip is moved to a "switching point" for the target cell, as defined herein. The tip penetrates the chorion of the target cell and deposits material into the cytoplasm of the target cell. The next cell is then brought into the field of view. The cell is recognized, and injection process is repeated until all cells in the batch are injected. In yet another aspect, the present invention provides a contact detection method to establish a home position for the injection means, e.g., a micropipette, in order to avoid unwanted contact between the micropipette tip and the cells when shifting between cells in the injection order. Upon retraction from the cell, the tip is moved to the home position.

The present invention allows for precise, highly reproducible deposition of foreign materials into a cell or a yolk of an embryo. Although the present description discusses depositing material into the cytoplasm center for embryos, it should be understood that the present invention is readily adaptable to allow for the deposition of material into other parts of a cell or embryo, as desired.

The present invention overcomes the problems of poor reproducibility, human fatigue, and low throughput inherent with traditional manual injection techniques. Besides automating cell injection by replacing human operation with high reliability and success rates, the present invention also provides high reproducibility and enables genuine high-throughput genetic research. The system and method have been implemented for the injection of zebrafish embryos, but can be readily extended to automated injection of other biological entities, such as mouse embryos, *drosophila* embryos, and *C. elegans*.

BRIEF DESCRIPTION OF THE DRAWINGS

A detailed description of the preferred embodiments is provided herein below by way of example only and with reference to the following drawings, in which.

Figure 1:
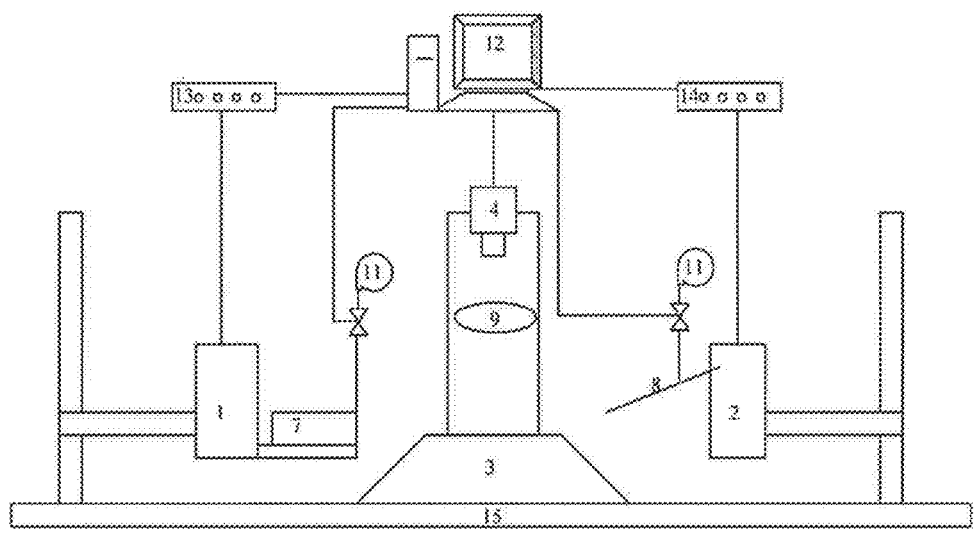
FIG. 1 illustrates a schematic diagram of components of the high-throughput automated cellular injection system.

In the drawings, one embodiment of the invention is illustrated by way of example. It is to be expressly understood that the description and drawings are only for the purpose of illustration and as an aid to understanding, and are not intended as a definition of the limits of the invention.

DETAILED DESCRIPTION OF THE INVENTION

With reference to FIG. 1, a system in accordance with the present invention comprises the following main components:

(i) Two motorized positioning devices (herein termed 'positioner') 1, 2, such as multi-DOF motorized positioning stages or microrobots/micromanipulators that control the motion of embryos and micropipette 8, respectively.

(ii) Control software unit running on a host computer 12 for motion control and image processing.

(iii) Positioner control device 13, 14 connected to or mounted on the host computer 12 to physically provide control signals to the two positioners 1, 2 and the pressure unit 11 (component viii).

(iv) An embryo holding device 7 placed on one positioner 1.

(v) An injection means in the form of a micropipette 8 (e.g., glass capillary or microfabricated needle) attached to the second positioner 2. The tip of the micropipette 8 is preferably about 100 to 800 µm long, and more preferably about 600 µm long, and preferably about 5 to 10 µm in diameter, as an example. The dimensions of a suitable injection means will vary depending on the structure of the target.

(vi) An optical microscope (objective 9 and base 3).

(vii) A CCD/CMOS camera 4 mounted on the optical microscope.

(viii) A computer-controlled pressure unit 11.

(ix) A vibration isolation table 15 to minimize vibration (optional).

Although this particular configuration of the system relates to the injection of material into zebrafish embryos, it should be expressly understood that this is an illustrative example only and the present invention is readily adaptable for the automated injection of other biological entities such as mouse embryos, *drosophila* embryos, and *C. elegans*, or any other appropriate cell as would be recognized and understood by a person of skill in the art. As would be appreciated by a person of skill in the art, the precise techniques of cell immobilization and cell structure would vary for different biological entities.

Figure 2:
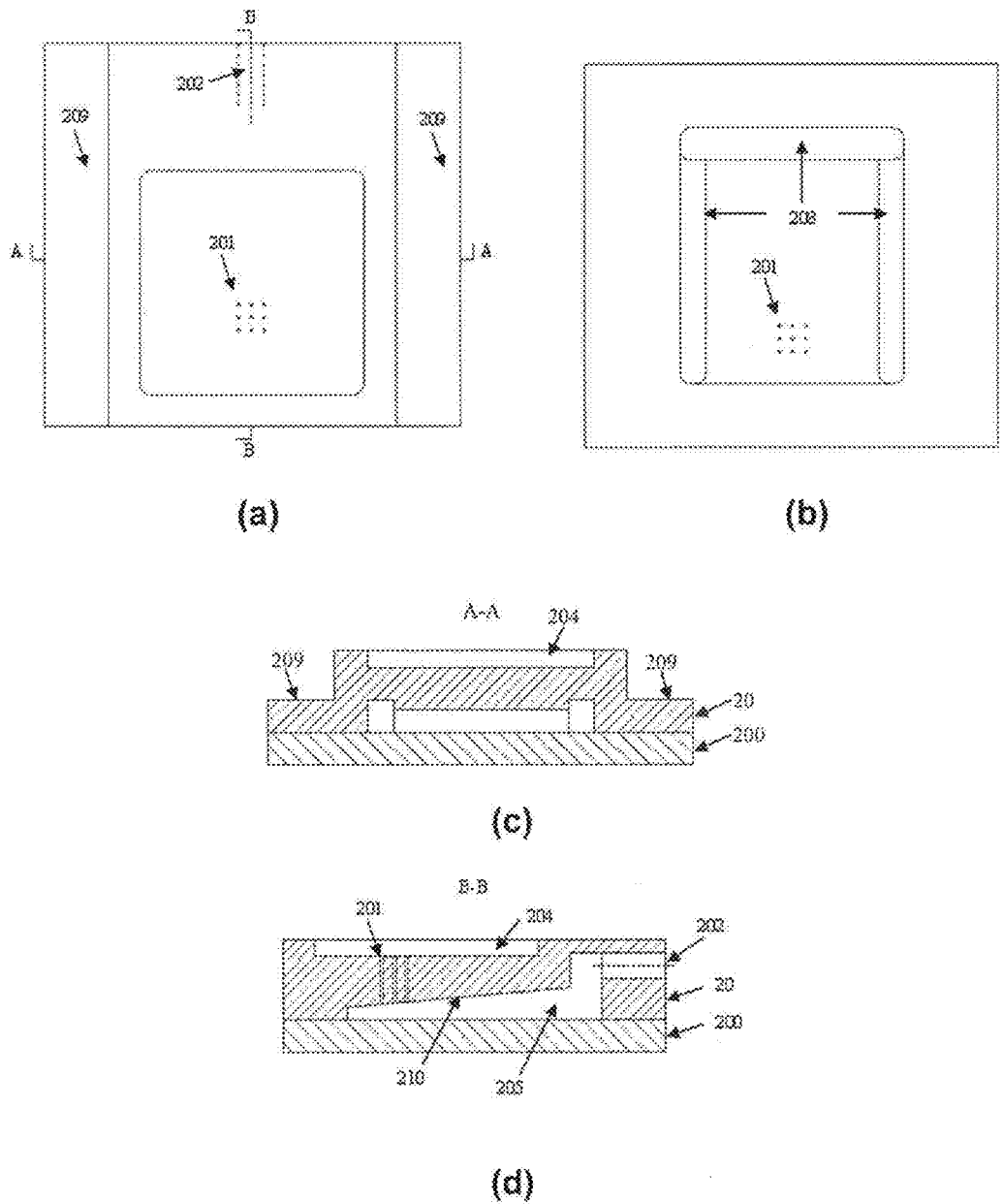
FIGS. 2(a)-(d) illustrate schematic diagrams of a zebrafish embryo holding device from a top view, bottom view, A-A section view and B-B section view, respectively.

An embryo holding device 7, either microfabricated or conventionally machined, is used to position a large number of zebrafish embryos into regular patterns. FIG. 2 shows one example vacuum-based device. The device described in FIG. 2 has two parts: embryo sucking structure 20, a flat piece 200 glued on the bottom of the embryo sucking structure 20. Arrays of through holes 201 are used to immobilize zebrafish embryos with negative pressure applied through the air outlet 202 on the side wall of the chamber 205. When a large number of zebrafish embryos are dispersed onto the device, each hole immobilizes a single embryo, and the non-trapped embryos are flushed away. Materials to use for constructing the cell holding device are ideally optically transparent, biocompatible, and easy for machining (e.g., polycarbonate).

The diameter of the through holes 201 is between 0.4 mm and 0.5 mm, for example. This through hole size is particularly suitable for zebrafish embryos. For mouse embryos, for example, the hole diameter would be smaller, about 20-40 µm, for example. Preferably, the negative pressure applied to immobilizing embryos should be low enough not to cause damage or negative effects for embryonic development. For example, the negative pressure is 0.5-7.5 InHg.

A reservoir 204 contains culture media/solution throughout the injection process. A slope 210 on the bottom surface of the holes 201 can be created in order for air bubbles to escape more readily such that they do not stick to the bottom surface. The three airflow channels 208 along the bottom surface are for inducing air to smoothly flow out of the chamber 205 via the air outlet 202. The air outlet 202 is positioned higher than the slope 210 to guarantee that the slope 210 is submerged in culture media/solution. The steps 209 are created such that the cell holding device can be fixed by two clamps under the microscope.

Figure 3:
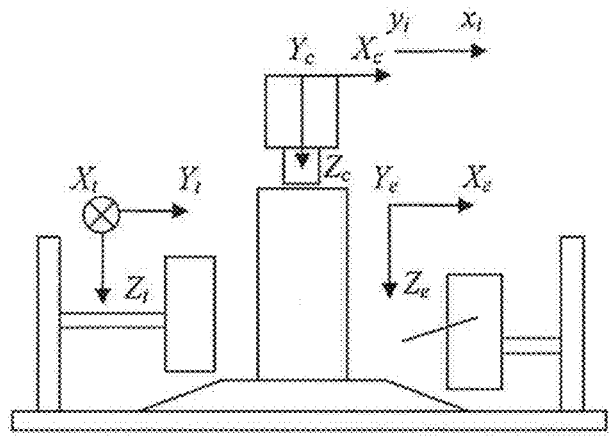
FIG. 3 illustrates coordinate frames in the present invention.
Figure 4:
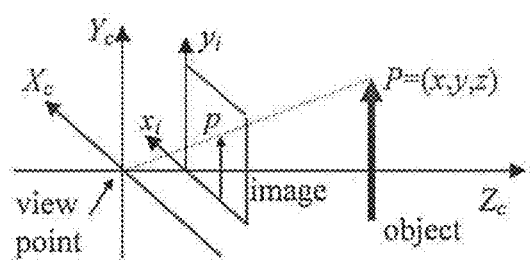
FIG. 4 illustrates an image projection model relating camera/image frames.
Figure 5:
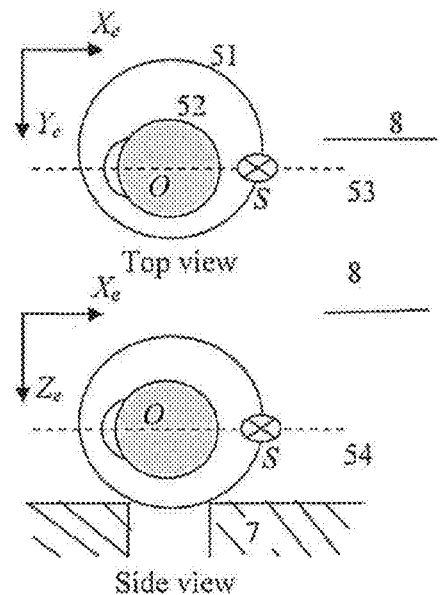
FIGS. 5(a)-(h) illustrate micropipette motion sequences for injecting each embryo.
Figure 5:
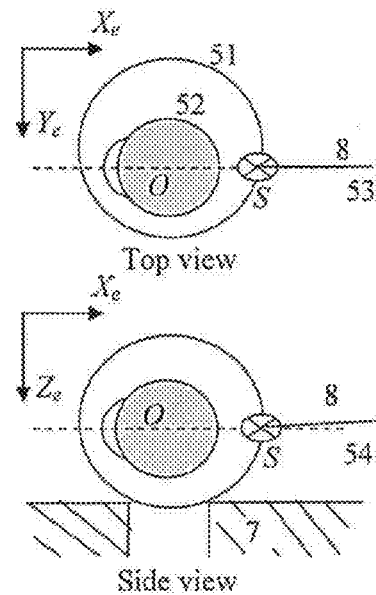
Figure 5:
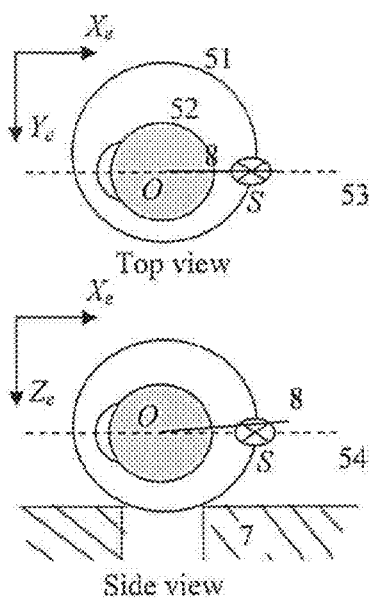
Figure 5:
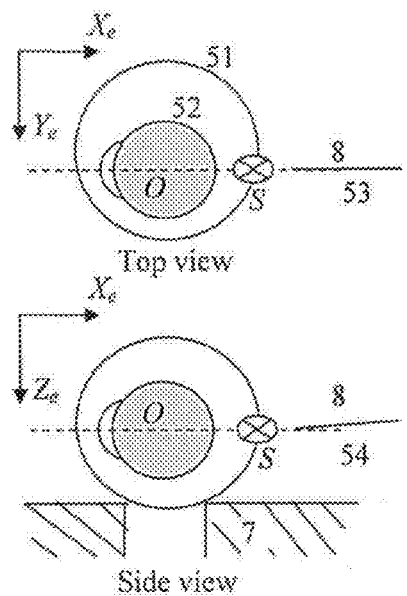
Figure 5:
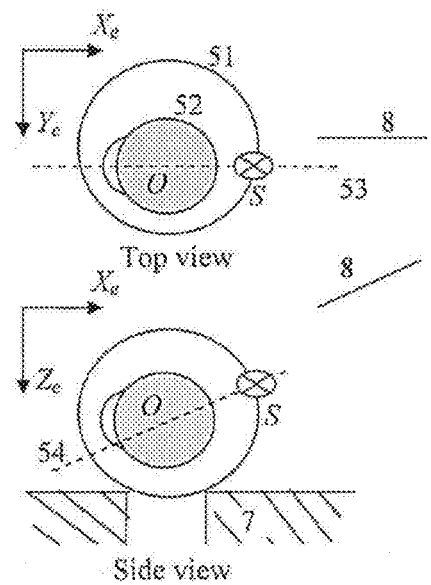
Figure 5:
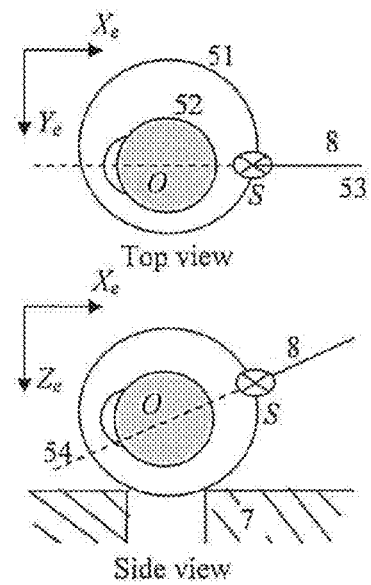
Figure 5:
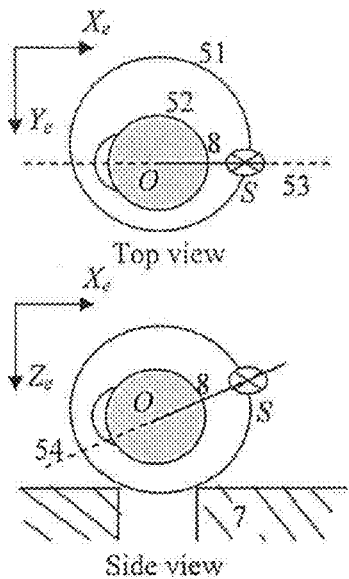
Figure 5:
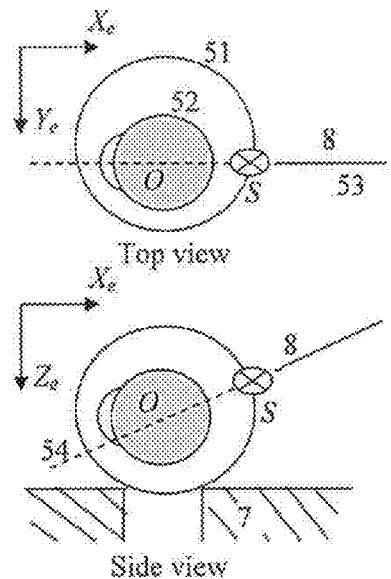

The coordinate frames of the system used in FIG. 3 and FIG. 4 are summarized in Table 1.

TABLE 1

Coordinate frames (FIG. 3 and FIG. 4) of the system.

| Symbol | Coordinate frame |
|---|---|
| e | End-effector coordinate frame $X_e$-$Y_e$-$Z_e$ attached to positioner 2 (micropipette 8 as the end-effector) |
| t | Target coordinate frame $X_t$-$Y_t$-$Z_t$ attached to positioner 1 that controls the motion of embryos |
| c | Camera coordinate frame $X_c$-$Y_c$-$Z_c$ |
| i | Coordinate frame $x_i$-$y_i$ (or x-y) for the image plane |

A point P=(x,y,z) in the camera frame $X_c$-$Y_c$-$Z_c$ is mapped to a point p=(u,v) in the image plane x-y via $$\begin{bmatrix} s_x & 0 \\ 0 & s_y \end{bmatrix} \begin{bmatrix} u \\ v \end{bmatrix} = \begin{bmatrix} x \\ y \end{bmatrix}$$

where $s_x$ and $s_y$ are fixed scale factors or pixel size in x-axis ($s_x$) and y-axis ($s_y$) respectively that can be either calibrated off-line manually or on-line automatically as discussed later. They will be referred to as s thereafter.

Overall Injection Method

A large number of zebrafish embryos are first positioned in a regular pattern on the embryo holding device 7. The embryos are brought into focus with an auto-focusing algorithm. A vision-based contact detection algorithm determines the vertical positions of the micropipette tip and the top surface of the holding device 7. Each embryo is recognized and centered in the field of view; simultaneously, the micropipette tip is moved to a switching point. The tip penetrates the chorion 51 and deposits genetic materials into the cytoplasm 52 of the target cell. Upon retreating out of the embryo, the tip is moved to the home position. In the meanwhile, the next embryo is brought into the field of view. The embryo is recognized, and injection process is repeated until all embryos in the batch are injected.

Micropipette Motion Control Sequence for Injecting Each Embryo

'Cytoplasm' in this invention refers to the combination of the yolk and the cells of an embryo, e.g., a zebrafish embryo. As shown in FIGS. 5(a)-(d), when the micropipette tip is nearly horizontal, the two principal planes 53 and 54 (crossing the cytoplasm center O, parallel to the $X_e$-$Z_e$ and $X_e$-$Y_e$ plane, respectively) overlap at two points. The point that is closer to micropipette 8 is referred to as the switching point S. The motion sequence of the micropipette 8 for injecting one embryo is as follows:

1. Move from home position (home position, described later in control flow 702 and 703, is above and to the right of the chorion 51) to the switching point S simultaneously along all three axes with positioner 2 (FIG. 5(b)). In the meanwhile, the embryo cytoplasm center O is brought to the center of the field of view by positioner 1.

2. Penetrate the chorion 51 and move to the cytoplasm center O along the $X_e$ direction only (FIG. 5(c)). Upon reaching center O, a pre-specified amount of genetic materials (e.g., DNA or morpholinos) is deposited by the computer-controlled pressure unit 11.

3. Retreat from the cytoplasm center O beyond the switching point S along the $X_e$ direction only (FIG. 5(d)).

4. Move to home position (FIG. 5(a)). Simultaneously, the next embryo is brought into the field of view by positioner 1.

This invention allows for precise, highly reproducible deposition of foreign materials into the cell or the yolk. The following description assumes that one desires to deposit foreign materials into the cytoplasm center for every embryo.

When the micropipette tip has a significant tilting angle (e.g., >5°) as shown in FIG. 5(e)-(h), micropipette motion control sequence can be made slightly different from the above-mentioned in order to minimize cellular damage. The two different steps are: (i) principal plane 54 still crosses cytoplasm center O but is parallel to micropipette tip 8 from the side view; and (ii) during penetration and retraction, the micropipette moves along the direction of its principle axes (FIG. 5 (g)-(h)), instead of purely along the $X_e$ direction.

Although the following description corresponds to the case shown in FIG. 5(a)-(d), the invention can also be implemented as shown in FIG. 5(e)-(h).

Injection Path Planning

Figure 6:
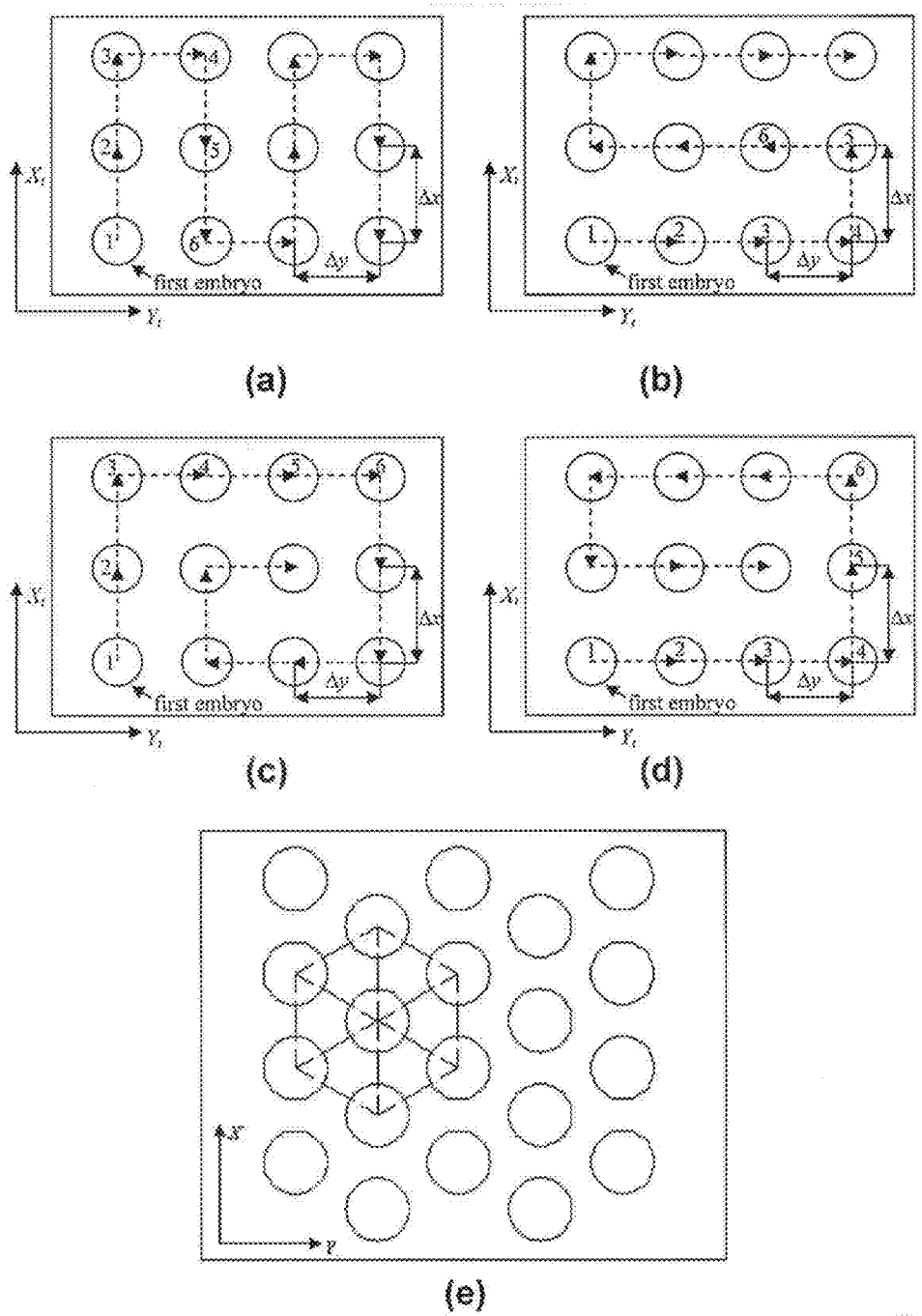
FIGS. 6(a)-(e) illustrate embryo injection sequences and through-hole configuration.

Denote the pitch (i.e., spacing between two adjacent holes 201) along the $X_t$ and $Y_t$ directions as $\Delta x$ and $\Delta y$. Denote the number of embryos along the $X_t$ and $Y_t$ directions as m and n. Starting with the first embryo (FIG. 6(a)-(d)), positioner 1 is controlled to travel along the path shown in dashed lines for sequential injection of the entire batch of embryos. Of the four paths when embryos are arranged in regular grids (most often m>2, n>2), given $\Delta y > \Delta x$, path 61 shown in FIG. 6(a) is the shortest. Given $\Delta x > \Delta y$, path 62 shown in FIG. 6(b) is the shortest. In the case of $\Delta y = \Delta x$, the four paths have the same total travel distance. In order to increase throughput, the shortest path should be taken.

The through holes 201 can also be arranged into other patterns other than those shown in FIG. 6(a)-(d). For example, every six nearest holes 201 to the middle one can be such configured that they form an equilateral hexagon (FIG. 6(e)). Such a configuration achieves a maximum number of holes for a given device surface area, which can be adopted for the purpose of maximizing the number of embryos for each batch.

Injection Control Flow

Figure 7:
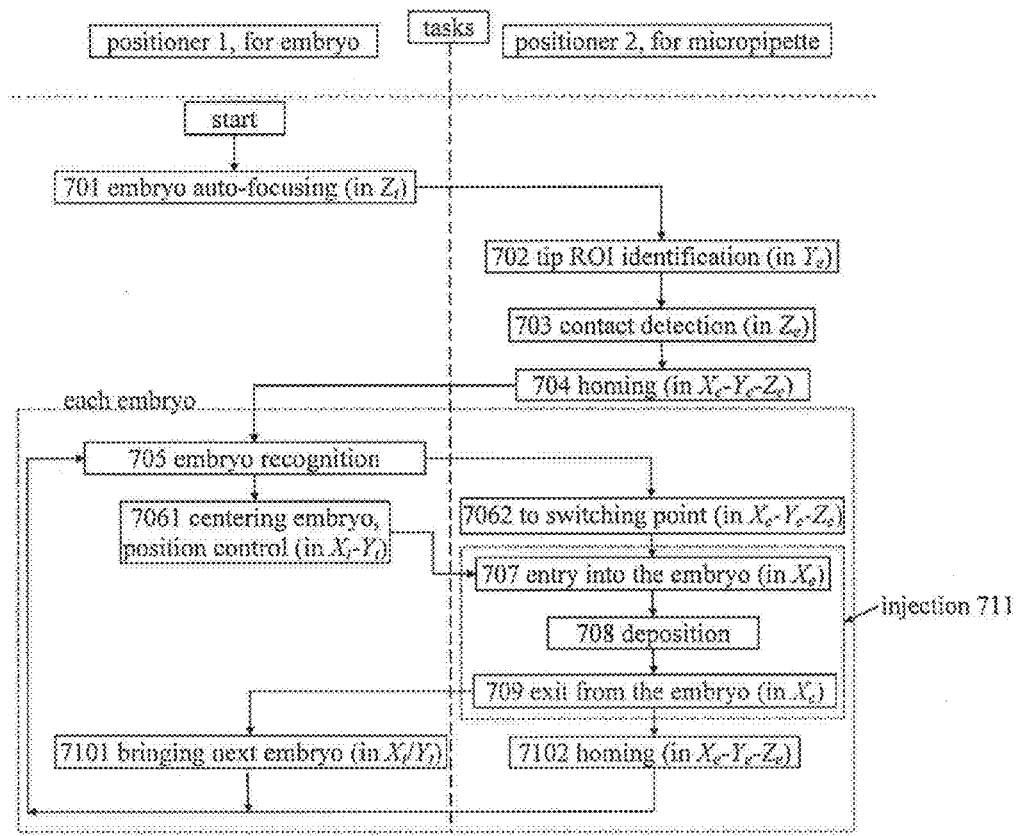
FIG. 7 illustrates automatic injection control flow.

After a batch of zebrafish embryos are immobilized on the cell holding device 7, fully automated operation starts according to the control flow as described in FIG. 7.

Embryo Auto-Focusing 701:

Prior to autonomous injection, the embryos need to be brought into focus. This auto-focusing step 701 only needs to be conducted once for each batch of embryos. Embryos are servoed by positioner 1 upwards (or downwards) by a certain distance (e.g., 5 mm) to cross the focal plane. An autofocusing algorithm (e.g., Tenenbaum gradient) is used to locate the focal plane by constantly calculating the focus measure for each frame of image. The embryos are moved to the focal plane that corresponds to the maximum (or minimum) focus measure.

Figure 8:
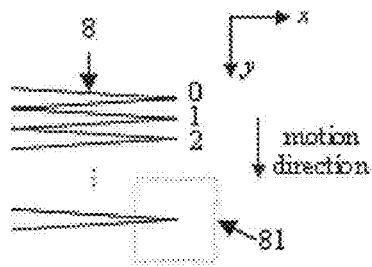
FIG. 8 illustrates a micropipette moving in the image plane.

Identification of Micropipette Tip ROI (Region of Interest) 702:

This step is to locate the tip of the micropipette 8 for use in contact detection 703. The micropipette 8 controlled by positioner 2 moves only along the $Y_e$ direction. The moving micropipette that stands out in the image subtracted from the background is recognized (i.e., a region of interest 81 around the tip of the micropipette, shown in FIG. 8 is identified). Upon identification, the coordinates of the tip both in the image plane x-y and in the end-effector frame $X_e$-$Y_e$-$Z_e$ are determined. The x-coordinate and y-coordinate in the image plane x-y, $X_e$-coordinate and $Y_e$-coordinate in the end-effector frame $X_e$-$Y_e$-$Z_e$ are taken as the lateral components of the home position of the micropipette tip.

Figure 9:
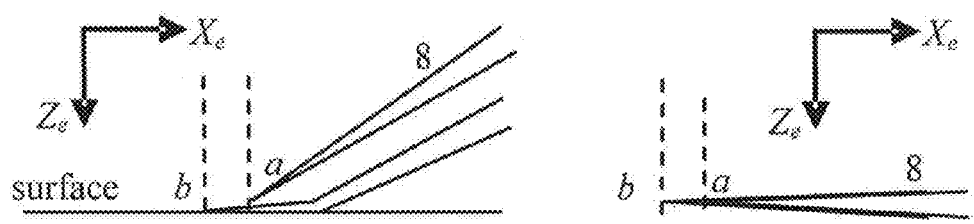
FIG. 9 illustrates contact between micropipette tip and embryo holding device.

Contact Detection 703 Using Computer Vision Feedback:

This step is to automatically align the tip of the micropipette 8 with the embryo cytoplasm center O in the vertical direction. In this procedure, the top surface of the cell holding device 7 serves as the reference plane. The micropipette 8 moves only along the $Z_e$ direction. Upon the establishment of the contact between the micropipette tip and the top surface, further vertical motion of the micropipette tip along the $Z_e$ direction results in lateral movement along the $X_e$ direction. As shown in FIG. 9, the micropipette tip is located at point a (initial contact) and b (after contact) in the surface plane. Before and after contact, the micropipette tip changes its x coordinate in the image plane x-y vs. time (i.e., image frame number), resulting in a V-shaped curve. The peak of the V-shaped curve represents the contact position along the vertical direction between the micropipette tip and the top surface of device 7.

After contact detection, the $Z_e$-coordinate of the switching point S is determined by moving upwards with respect to the contact position by half of the embryo diameter, e.g., 0.5-0.6 mm. The $Z_e$-coordinate of the home position of the micropipette tip is determined by moving upwards with respect to the contact position by the embryo diameter, e.g., 1.0-1.2 mm.

Upon the completion of 702 and 703, the home position of the micropipette tip both in the x-y image plane and the $X_e$-$Y_e$-$Z_e$ frame has been automatically determined and will be fixed for use in the following procedures of injecting all embryos within the batch.

Moving to the Home Position 704:

After 702 and 703, positioner 2 following a position control law (e.g., PID) moves the micropipette tip upwards and laterally to its home position determined in 702 and 703 from the vertical contact position in order to prevent the micropipette from crashing with embryos in between injections.

Figure 10:
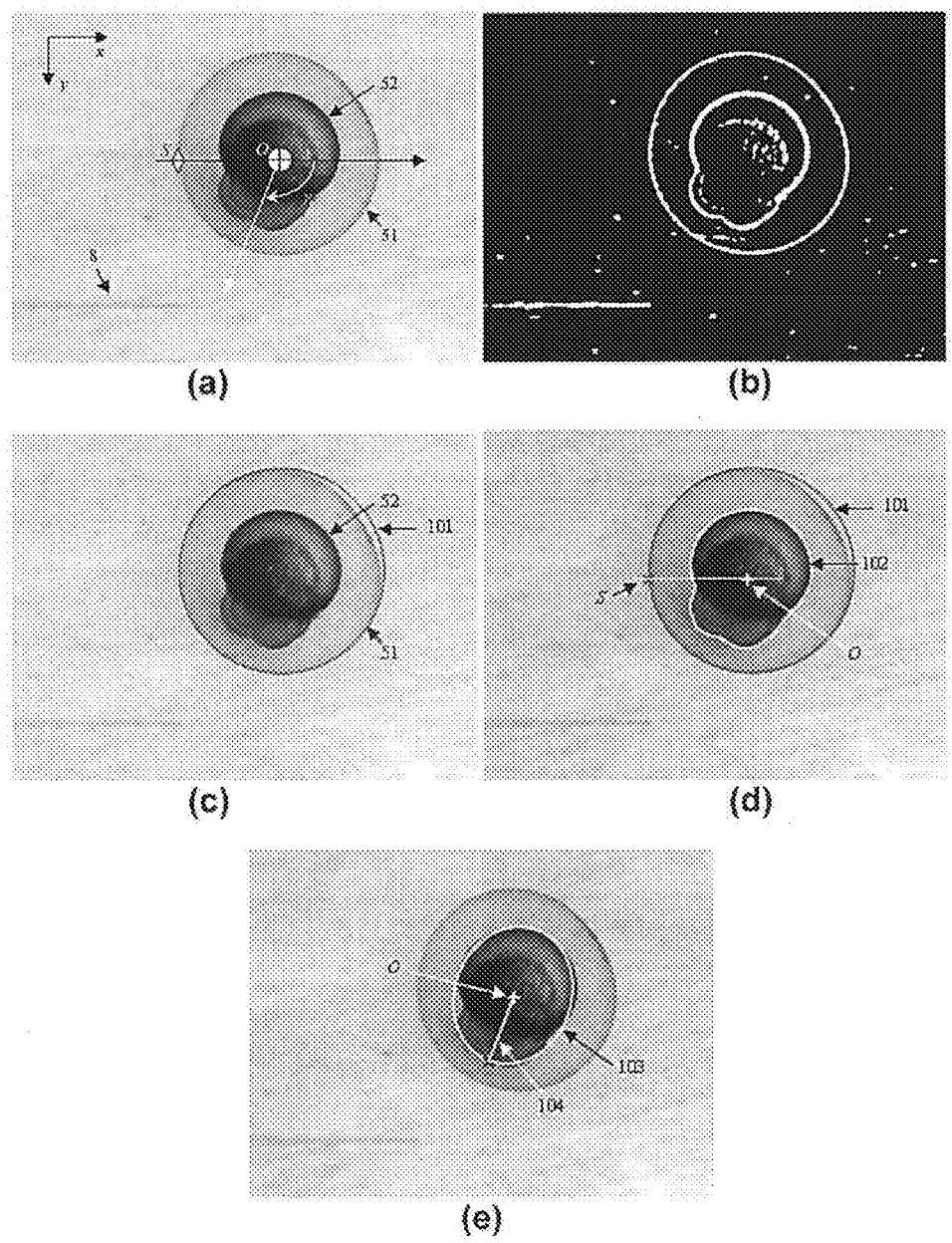
FIGS. 10(a)-(e) illustrate image processing steps for embryo structure recognition.

Embryo Recognition 705:

The objectives of this step are to identify the cytoplasm center O (FIG. 10(a)), the distance from the center O to the switching point S along the x direction, and the injection angle γ between the x axis and the principal axis 104 (FIG. 10(e)).

The embryo recognition steps are summarized in Table 2. The complete recognition process typically takes 16 ms on a PC (3.0 GHz CPU and 1 GB memory).

TABLE 2

| Embryo recognition 705. | |
| --- | --- |
| Step # | Processing |
| 1 | Pre-processing |
| 2 | Chorion 51 recognition |
| 3 | Cytoplasm 52 recognition |
| 4 | Determination of injection angle γ |

(1) Pre-processing. This step is to obtain a de-noised binary image. The image is first convolved with a low-pass Gaussian filter for noise suppression. Then the gray-level image is binarized to a black-white image using an adaptive thresholding method (e.g., setting a local threshold for each pixel as the mean value of its local neighbours). The binary image is eroded to remove small areas that are not of interest and then, dilated to connect broken segments that originally belong to one object. An example image after pre-processing is shown in FIG. 10(b).

(2) Chorion 51 recognition. Of many connected objects in the binary image, the one with the maximum area is taken as the chorion 51. In FIG. 10(c), the chorion 51 is circumvented by its minimum enclosing circle 101.

(3) Cytoplasm 52 recognition. The second largest object in the image shown in FIG. 10(b) is the cytoplasm 52. Its boundary is represented by a chain code contour. In some cases, the boundary of the cytoplasm 52 is not fully connected (i.e., a rotated 'C' shape with an opening other than a fully closed 'O' shape). Thus, a convex hull of the contour is used for further processing.

A region R is convex if and only if for any two points $x_1$, $x_2 \in R$, the complete line segment $x_1 x_2$ with end points $x_1$ and $x_2$ is inside the region R. The convex hull of a region is the smallest convex region H that satisfies the condition $R \subseteq H$.

The constructed convex hull of the contour serves as the initial curve for 'snakes', which will form a closed curve that represents the contour of cytoplasm 52. The obtained closed contour 102 by snake tracking is shown in FIG. 10(d). The centroid of the contour is recognized as the cytoplasm center O.

The switching point S is then determined as the intersect point of the minimum enclosing circle 101 and the horizontal line passing through the cytoplasm center O, as shown in FIG. 10(d).

(4) Determination of injection angle γ. Fitting the contour 102 of the cytoplasm 52 into an ellipse 103 using a least squares method results in the major axis of the fitted ellipse 103, which is taken as the principal axis 104 (FIG. 10(e)).

Figure 11:
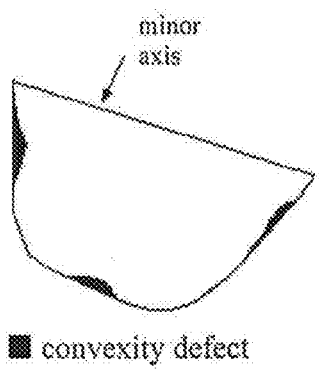
FIG. 11 illustrates convexity defects between the cell contour and its convex hull.

In order to determine the injection angle γ that represents the cell orientation, the yolk and the cell must be distinguished. The contour 102 is intercepted into two parts (cell part and yolk part) by the minor axis of the fitted ellipse 103. Define the area difference between a contour and its convex hull as the convexity defect. The convexity defects (FIG. 11) for the yolk part and cell part are calculated. Based on the fact that the yolk part always has a much more circular shape than the cell part (i.e., smaller defect), the contour with a greater defect is recognized as the cell part, thus, the cell part and yolk part are recognized. FIG. 10(e) shows the principal axis 104 starting from the cytoplasm center O(+) and ending on the cell contour (x). The injection angle γ is the angle between the x axis and the principal axis 104. As the injection angle γ represents cell orientation, the recognition of γ can also be important for automatically rotating embryos. For example, the angle can be constantly recognized in each frame of image as visual feedback for rotating an embryo such that the yolk part or the cell part can be rotated closed to or away from the micropipette tip.

The following two tasks 7061 and 7062 are performed in parallel after task 705.

Centering Embryo 7061:

According to calibrated pixel size s and the distance between the cytoplasm center O and the image center in the image plane, positioner 1 is controlled with a position control law to move the embryo into the image center.

Moving the Micropipette Tip to Switching Point 7062:

In parallel with centering embryo 7061, the micropipette 8 is then moved by positioner 2 from home position to the switching point S by a position control law (e.g., PID).

Entry into the Embryo 707:

The micropipette tip is controlled to start from the switching point S to arrive at the cytoplasm center O by a position control law at an appropriate speed that does not cause embryo lysis.

Genetic Material Deposition 708:

Based on a desired deposition volume, the micropipette tip size (inner diameter) and specified injection pressure level determine the positive pressure pulse length (i.e., pressure 'on' time). Injection pressure is maintained high for the determined time period through the computer-controlled pressure unit 11, precisely depositing a desired volume of genetic materials at the cytoplasm center O.

Exiting from the Embryo 709:

Controlled by positioner 2, the micropipette 8 is retracted out of the embryo by a position control law at an appropriate speed that does not cause embryo lysis.

The following two tasks 7101 and 7102 are performed in parallel.

Moving the Next Embryo into the Field of View 7101:

This step brings the next embryo into the field of view (the image plane x-y) according to the pitches between adjacent through holes 201 of the embryo holding device 7. Traveling the relative displacement (Δx or Δy) is executed by an appropriate position control law, driven by positioner 1.

Moving Micropipette to the Home Position 7102:

In parallel with bringing the next embryo into the filed of view 7101 with positioner 1, positioner 2 following a position control law moves the micropipette tip upwards and laterally to its home position determined in 702 and 703.

Figure 12:
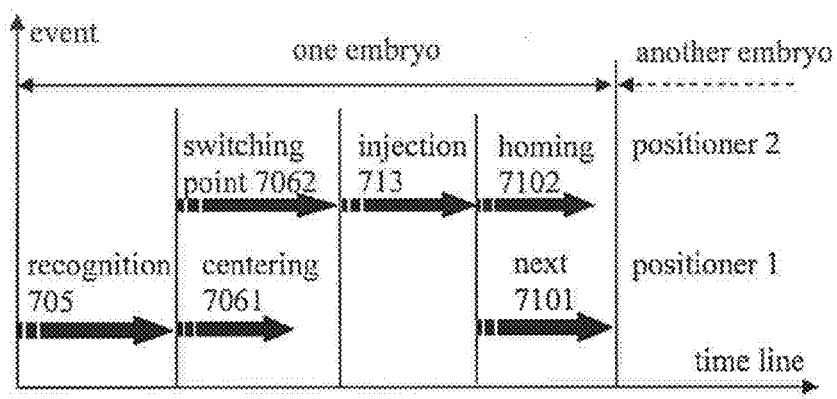
FIG. 12 illustrates parallel task execution of the two positioners.

Repeat 705-7061-7062-707-708-709-7101-7102 for Each Embryo:

In order to achieve the highest throughput, for injecting each embryo, the two positioners 1, 2 perform tasks in parallel whenever possible, as shown in FIG. 12. Performing tasks in parallel operation is an effective approach to enhance the efficiency of the system.

An Alternative Injection Control Flow

The control flow described in FIG. 7 requires a prior knowledge of pixel size s that is obtained through off-line pixel size calibration. The pixel size s varies with different microscopy magnifications that are typically determined by microscope objectives, couplers, and the camera. In order to eliminate the magnification/hardware dependence, on-line calibration can be conducted to automatically determine the pixel size. Accordingly, the control flow is modified (FIG. 13), particularly, for the operation on the first embryo when on-line pixel calibration is conducted.

Figure 13:
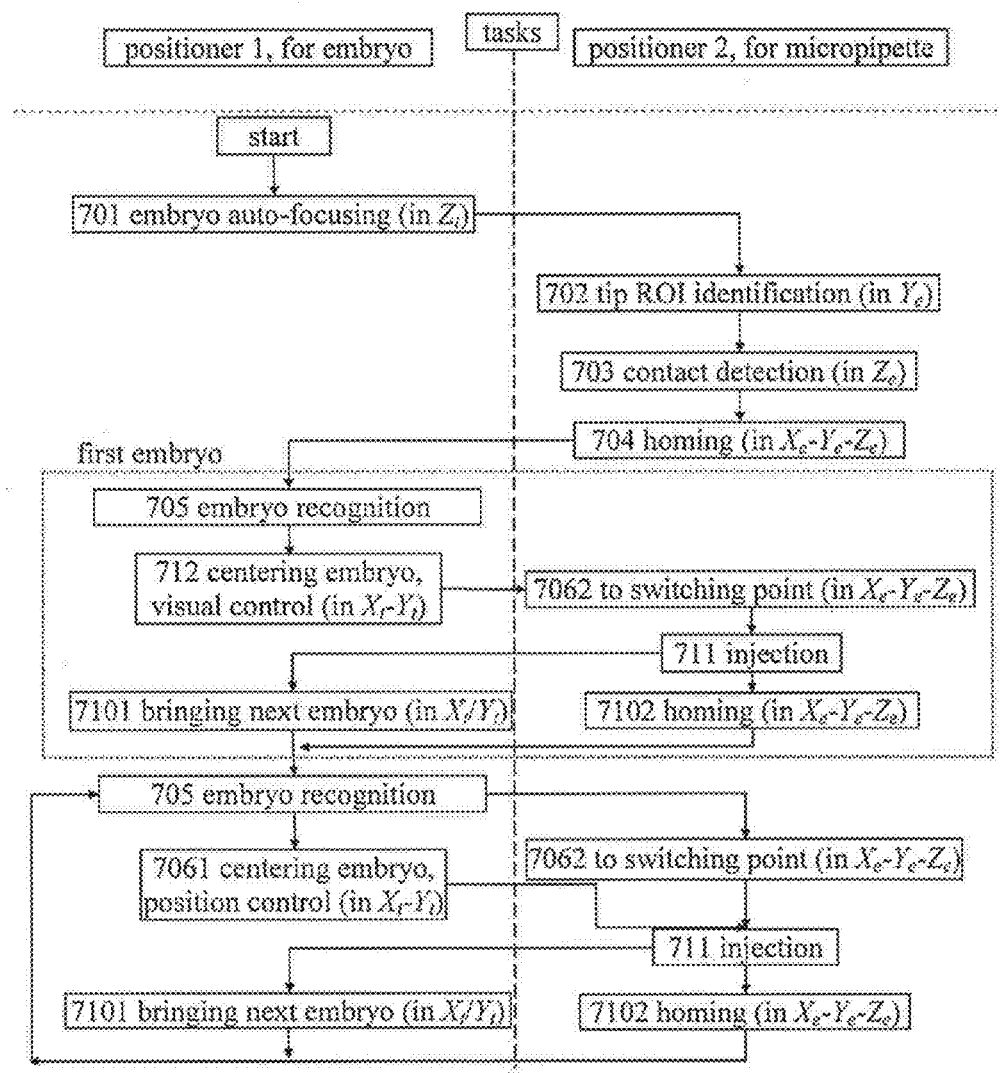
FIG. 13 illustrates alternative injection control flow with an on-line pixel size calibration step.

Comparing the control flow shown in FIG. 7 and the flow shown in FIG. 13, one can see that 7061 is replaced with task 712. Also note that 712 is not performed in parallel with 7062.

Centering Embryo, Visual Servo Control 712:

Unlike 7061, 712 visually servos the cytoplasm center O to the center of the field of view. The cytoplasm center O recognized in step 705 is selected as the image feature for tracking and a visual tracking method (e.g., sum-squared-difference) is applied. The cytoplasm center O is continuously tracked, providing visual feedback to the image-based visual servo control loop. Based on the visual tracking results (i.e., pixel displacement in the image plane x-y) and the position feedback from positioner 1 (i.e., travelling distance in the frame $X_t$-$Y_t$-$Z_t$), the pixel size s is calibrated on line.

System Robustness Enhancement

Error-free operation is critical to warrant the commercial viability of the system. From the perspective of robustness enhancement, the system features an error protection mechanism. Table 3 summarizes potential errors that can occur during operation and their detection methods. When any error is detected, the system is halted with alarms sounded to alert the user and detailed error messages reported to the user.

In control software design that implements the control flow described in FIG. 7 or FIG. 13, the detection methods must also be implemented as integrative components for system robustness enhancement.

rent operation status (different color indicates completed, on-going, or to be conducted).

It will be appreciated by those skilled in the art that other variations of the preferred embodiment may also be practiced without departing from the scope of the invention.

The high-throughput automated cellular injection system described herein has at least the following general advantages:

i) high success rate;
ii) high reproducibility (because the embryo structure is fully recognized, the deposition target can be selected other than the cytoplasm center O);
iii) high-throughput;

TABLE 3

Potential errors and corresponding detection methods.

| Error description | Detection method |
|---|---|
| 1. Hardware problems: failure in establishing communication with controllers, error in positioner control device, etc. | Query camera, positioner control device, communication channel upon launching the control software. |
| 2. Lighting problem: light off or poor illumination | Calculate the average gray-level and standard deviation of a random frame of image. If the two parameters are both lower than a pre-set threshold value, for example, both are too low, lighting problem most probably exist. |
| 3. Failure in detecting micropipette tip ROI in 702 | In most cases, within several frames (e.g., 5–10, depending on the positioner 2 speed and microscopy magnification) the micropipette tip can be detected. If the tip is not detected within 20 frames of images, failure most probably has occurred. |
| 4. Error in contact detection 703 | The micropipette tip can be too small a feature to be recognized with a noisy background. If the tip cannot be constantly detected in any frame of image when the tip is being lowered down, an error should have occurred. |
| 5. Embryo recognition error | In each of the following cases, an error is detected:<br>(1) If the radius of the minimum enclosing circle for the chorion is too large, for example, exceeding half of the image width in pixel, or is too little.<br>(2) If the recognized cytoplasm center is outside the minimum enclosing circle.<br>(3) If the recognized cytoplasm center is too close to the chorion.<br>(4) If the fitted ellipse of the cytoplasm contour has a minor axis greater than $2/3$ diameter of the minimum enclosing circle. |
| 6. Micropipette tip clogging | After injecting a number of embryos (e.g., a batch of 25), micropipette clogging should be inspected. The pressure unit 11 pushes genetic materials (e.g., DNA) out of the micropipette tip to form a sphere. Based on image processing, if no sphere is formed or a reduced radius is identified compared to the clogging-free case, clogging should have occurred. Alternatively, for each embryo within a batch, negative pressure applied by the pressure unit 11 can be measured constantly (e.g., with a pressure sensor integrated in the pressure path), an abnormal pressure value indicates partial or complete clogging of the micropipette. Using the pressure monitoring approach, micropipette breakage can also be detected. |
| 7. Micropipette buckling | Buckling can occur under one of the following conditions: (1) micropipette tip is misaligned with the embryo; (2) embryo is not fully immobilized; (3) in rare cases, chorion of the embryo is exceptionally stiff and much harder to penetrate. Micropipette buckling can be detected by visually monitoring if the micropipette contour changes from a straight line to a curve pattern. |
| 8. Reaching motion limit of positioners | The first method is to constantly check the position feedback from the positioners. The second method is to monitor overall image changes when the positioners are supposed to move. Little or no image pattern changes indicate that the positioners could have reached limit. |
| 9. On-line calibration error | Before on-line calibration is conducted, if the cytoplasm center of the first embryo is exactly at or extremely close to the image plane center, on-line calibration can result in significant error (divide-by-zero). |

Figure 14:
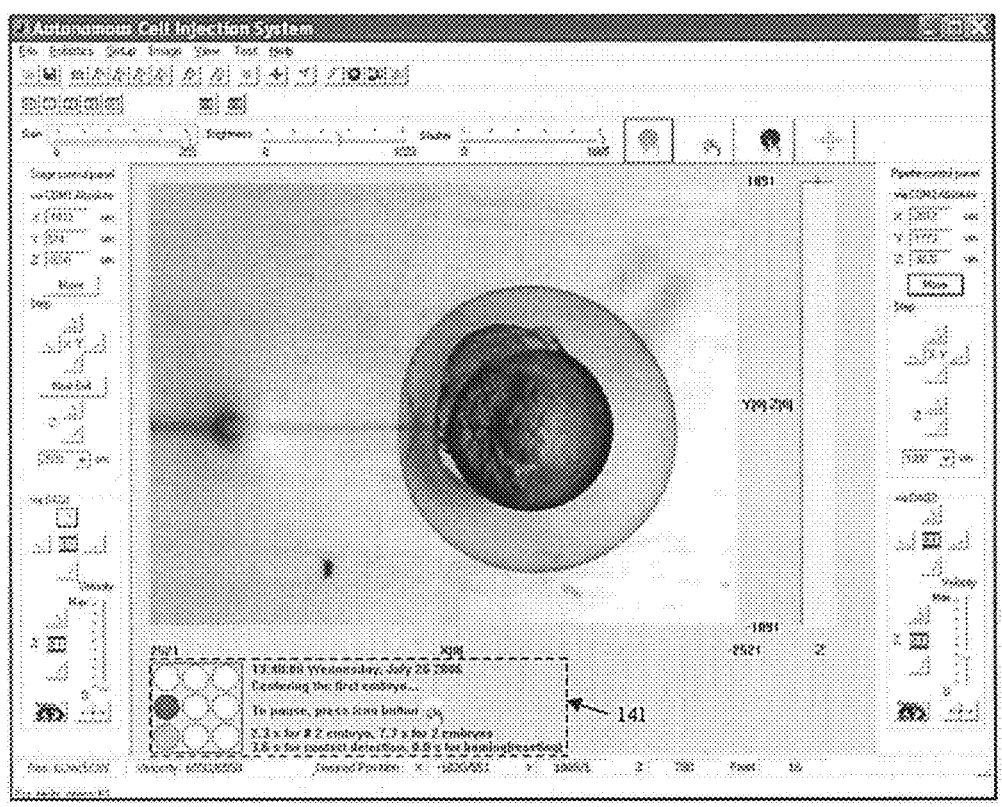
FIG. 14 illustrates an example control program interface.

The system is capable of automatically inject embryos sequentially for a complete batch. It also allows only injecting selected embryos within a batch. For example, in one user-friendly control interface shown in FIG. 14, area 141 provides an interactive means for the user to select embryos from a batch for injection by clicking the circles (circle positions correspond to embryo positions), besides displaying the curiv) fast embryo immobilization;
v) low-cost, biocompatible, optically transparent embryo holding device that produces high image quality for image processing/pattern recognition;
vi) fully automatic contact detection, facilitating precise alignment of the micropipette tip and embryo center in height;

vii) optimized embryo injection path to shorten positioners' total travel distance;
viii) robust image processing methods;
ix) optical platform (e.g., microscopy magnification) independence, enabled by the on-line pixel size calibration technique;
x) automated, precise material deposition using a computer controlled pressure unit;
xi) enhanced robustness due to error detection mechanisms; and
xii) user-friendly control program interface providing operation flexibility and process monitoring.

What is claimed is:

1. A system for automated cellular injection comprising:
(a) a multi-degree-of-freedom motorized positioner stage control device operable to control motion of a multi-degree-of-freedom motorized positioner stage, the multi-degree-of-freedom motorized positioner stage connected to a multicellular holding device operable to immobilize a batch of more than one cell in a desired position, the holding device being made of a biocompatible and optically transparent material;
(b) a multi-degree-of-freedom micromanipulator control device operable to control motion of a multi-degree-of-freedom micromanipulator, the multi-degree-of-freedom micromanipulator connected to a micropipette, the micropipette having a tip;
(c) a pressure unit connected to the micropipette, the pressure unit operable to pass a deposition volume of a material at an injection pressure to the micropipette;
(d) a microscope means comprising a camera mounted on an optical microscope for viewing the position of the micropipette relative to the holding device; and
(e) a host computer that includes control software for computer-controlled motion control and for computer-controlled image processing, said host computer being capable of automatically controlling the multi-degree-of-freedom motorized positioner stage control device, the multi-degree-of-freedom micromanipulator control device, the pressure unit and the microscope means;
wherein the computer-controlled image processing enables the host computer to automatically align the tip of the micropipette with cells within the batch of more than one cell;
wherein the computer controlled motion control enables the host computer to automatically inject materials sequentially into cells of the batch of more than one cell through the tip of the micropipette; and
wherein the control software comprises contact detection means which includes instructions that, when executed, automatically determine the position of the tip of the micropipette and a surface of the biocompatible and optically transparent holding device.

2. The system for automated cellular injection of claim 1 wherein the micropipette is a glass capillary or microfabricated needle having a tip length and an inner diameter operable for injecting the materials into the one or more cells.

3. The system for automated cellular injection of claim 1 wherein the camera is a coupled-charge device (CCD) or a complementary-metal-oxide-semiconductor (CMOS) camera.

4. The system for automated cellular injection of claim 1 further comprising a vibration isolation table to minimize vibration.

5. The system for automated cellular injection of claim 1 wherein, the cells in the batch are non-adherent cells.

6. The system for automated cellular injection of claim 1 wherein the more than one cell in the batch are embryos.

7. The system for automated cellular injection of claim 1 wherein the holding device is vacuum-based.

8. The system for automated cellular injection of claim 1 wherein the holding device includes (i) a reservoir to contain a cell culture media solution and the batch of more than one cell, (ii) an air flow channel for connection to a source of negative pressure, and (iii) an array of through holes disposed on a surface of the reservoir, each through hole having a top opening sized to receive one cell and a bottom opening, the air flow channel being in fluid communication with the reservoir through the openings of the through holes.

9. The system for automated cellular injection of claim 8, wherein the bottom opening includes a surface having a tilting slope, wherein the tilting slope is structural property of the bottom opening.

10. The system for automated cellular injection of claim 1, wherein the cells in the batch are automatically injected with the material according to a selective path sequence, and wherein the selective path sequence is automatically optimized such that the total distance of movement of the multi-degree-of-freedom motorized positioner stage is minimized.

11. The system for automated cellular injection of claim 1 wherein injection of the cells in the batch is achieved via position control algorithm.

12. The system for automated cellular injection of claim 1 wherein the control software includes image processing means including instructions that, when executed, operate to cause the host computer to automatically: (a) pre-process a cellular image to obtain a de-noised image; (b) determine an outer diameter for the cells in the batch; (c) approximate a cytoplasm center for the cells in the batch; (d) determine a switching point for the cells in the batch, the switching point being the intersect point of the outer diameter of a cell and an horizontal line passing through the cytoplasm center the cell; and (e) where the cells in the batch are embryos, distinguishing a cell and a yolk part, wherein an injection angle for the micropipette is recognized in substantially real-time.

13. The system for automated cellular injection of claim 12 wherein the image processing means include instructions that, when executed, operate to cause users to select a specific site within the cells in the batch, for automatic injection of the cells to said specific site.

14. The system for automated cellular injection of claim 12 wherein the image processing means includes instructions that, when executed, operate to cause the host computer to automatically determine pixel size, wherein the pixel size can be on-line calibrated with a visual servo control means.

15. The system for automated cellular injection of claim 1 wherein, the multi-degree-of-freedom motorized positioner stage and the multi-degree-of-freedom micromanipulator are controlled to execute tasks simultaneously to increase throughput.

16. The system for automated cellular injection of claim 1 wherein the control software includes error detection means.

17. The system for automated cellular injection of claim 1 wherein the control software includes a user responsive system.

18. The system for automated cellular injection of claim 1 wherein the system is capable of automatically injecting all of the cells in the batch sequentially or sequentially injecting selected cells within the batch of cells.

19. The system for automated cellular injection of claim 1 wherein the computer-controlled motion control include instructions that, when executed, operate to cause the host computer to automatically control entry and retraction of the micropipette into the cells to minimize damage to the cells.

20. The system for automated cellular injection of claim 1 wherein the cells are zebrafish embryos.

21. The system for automated cellular injection of claim 16, wherein the error detection means includes means for detecting one or more errors from the group consisting of hardware problems, lighting problems, detecting failure of the tip of the micropipette, contact detection error, embryo recognition error, clogging of the micropipette tip, buckling of the micropipette, reaching motion limit of the multi-degree-of-freedom motorized positioner stage or the multi-degree-of-freedom micromanipulator, or on-line calibration error.

22. The system for automated cellular injection of claim 5 wherein the cells are zebrafish embryos.

23. The system for automated cellular injection of claim 1, wherein the host computer controls the multi-degree-of-freedom micromanipulator to inject the cells in the batch along a shortest injection path.

* * * * *